(12) United States Patent
Cheng et al.

(10) Patent No.: US 8,268,012 B1
(45) Date of Patent: Sep. 18, 2012

(54) FOUR-BAR-LINKAGE BRAKE-INCLUDED KNEE JOINT

(75) Inventors: Chia-Pao Cheng, New Taipei (TW); Fu-Kuo Wu, New Taipei (TW)

(73) Assignee: Ken Dall Enterprise Co., Ltd., New Taipei (TW)

( * ) Notice: Subject to any disclaimer, the term of this patent is extended or adjusted under 35 U.S.C. 154(b) by 22 days.

(21) Appl. No.: 13/072,778

(22) Filed: Mar. 28, 2011

(51) Int. Cl.
*A61F 2/64* (2006.01)
*A61F 2/68* (2006.01)

(52) U.S. Cl. ........................................................ 623/44

(58) Field of Classification Search ............... 623/43–45
See application file for complete search history.

(56) References Cited

U.S. PATENT DOCUMENTS

| | | | |
|---|---|---|---|
| 6,355,071 B1* | 3/2002 | Cheng | 623/45 |
| 6,749,640 B1* | 6/2004 | Luhrs et al. | 623/39 |
| 2006/0259153 A1* | 11/2006 | Harn et al. | 623/44 |
| 2011/0270415 A1* | 11/2011 | Chen et al. | 623/44 |

\* cited by examiner

*Primary Examiner* — Bruce E Snow
(74) *Attorney, Agent, or Firm* — Leong C. Lei

(57) ABSTRACT

A four-bar-linkage brake-included knee joint includes a knee carriage, first and second links rotatably coupled to the carriage, and a clamp member coupled to a joint body. The clamp member forms a through hole that receives an axle to couple the second links. A compression block is received in a rear portion of the joint body and is set in engagement with a back side of the clamp member. The clamp member forms a gap extending from the through hole of the clamp member to a bottom of the clamp member. When a heel of a prosthesis that includes the knee joint is put on the ground, a reaction force is induced in the prosthesis that causes the compression block to directly depress the clamp member thereby reducing the gap to have the clamp member tightly clamping the axle and thus preventing the axle from further rotation.

3 Claims, 10 Drawing Sheets

FOUR-BAR-LINKAGE BRAKE-INCLUDED KNEE JOINT

(a) TECHNICAL FIELD OF THE INVENTION

The present invention generally relates to a four-bar-linkage brake-included knee joint, which uses body weight or reaction forces induced by an artificial limb contacting the ground to reduce a gap formed in a clamp member for constraining rotation of axle thereby eliminating the potential risk caused by sudden bending of prosthesis knee joint in a standing or walking condition.

(b) DESCRIPTION OF THE PRIOR ART

A good prosthesis knee joint provides different supports to gravity center and associated cushioning. Also, the prosthesis knee joint requires a safety structure to provide protection against potential risk caused by sudden bending of the joint in a walking condition or in a process of changing the location of gravity center.

As shown in FIG. 7 of the attached drawings, a prosthesis user is often capable of steadily hold and support the body weight with the feet in a standing condition where the knee joint does not bend. With the extension of the time period when the prosthesis user is standing, it often desired to slightly bend the knee joint or to change the location of gravity center to take a comfortable standing posture in order to release the pressure locally acting on the knee joint. FIG. 8 shows a conventional four-bar-linkage prosthesis knee joint, which is capable of steadily supporting the body weight in a non-bending standing condition. However, when the user shifts the gravity center from the natural limb side to the artificial limb side, it is quite easy for the knee joint to make a sudden bending in the clockwise direction, leading to potential risks. Another situation where a similar sudden bending may occur is illustrated in FIGS. 9 and 10. In case that the prosthesis users is walking on a horizontal surface or a downhill slope, when the heel of the artificial limb in put on the ground, a force induced on the sole is transmitted upward along the limb. Under this condition, if the prosthesis user shifts the gravity center to the artificial limb side, the knee joint may make a sudden bending in the clockwise direction that may potentially cause a risk. Apparently, the conventional four-bar-linkage prosthesis knee joint needs to be further improved.

SUMMARY OF THE INVENTION

The present invention provides a four-bar-linkage brake-included knee joint. The knee carriage forms a front through hole and a rear through hole, the knee carriage and comprises an inner connection rod arranged inside the knee carriage to connect a cushioning assembly. A joint body has a front portion forming a joint body bore and has a rear portion in which a compression block is arranged. Two first links have upper ends coupled to the front through hole of the knee carriage and lower ends coupled to the joint body bore. Two second links have upper ends coupled to the rear through hole of the knee carriage. A clamp member is arranged at inner sides of the first links and the second links and has an upper portion forming an upper through hole and forms a lower through hole in a lower portion of a front portion thereof. The upper through hole receives an axle extending therethrough to couple to lower ends of the second links. The lower through hole is substantially in alignment with the joint body bore. The clamp member is set in such a way that a back side thereof is in engagement with the compression block that is arranged in the rear portion of the joint body. The upper through hole is provided with a gap, which comprises at least one bent segment and extends downward from the upper through hole to a bottom of the clamp member to have an opening thereof formed between the lower through hole and the clamp back.

In view of the drawbacks of the conventional four-bar-linkage prosthesis knee joint that are discussed above, the present invention aims to provide a four bar linkage for prosthesis, which comprises a clamp member, whereby when the user of the prosthesis takes an easy standing posture by slightly bending the knee or attempts to shift the gravity center to the artificial limb side, the body weight and a force induced in the lower portion of the prosthesis and transmitted upward work together to cause a compression block that is arranged in a rear portion of a joint body to directly depress a clamp back. This makes a gap formed in the clamp member reduced to have the clamp black tightly clamping the axle to prevent further rotation. When the prosthesis is walking on a horizontal surface or on a downhill slope, an upward force induced by the contact of the heel of the prosthesis with the ground may also be applied to cause the compression block that is arranged in the rear portion of the joint body to directly depress the clamp back. Again, the axle can be tightly clamped and further rotation is prevented, so that a potential risk of falling caused by sudden bending of the prosthesis knee joint in the clockwise direction can be eliminated.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
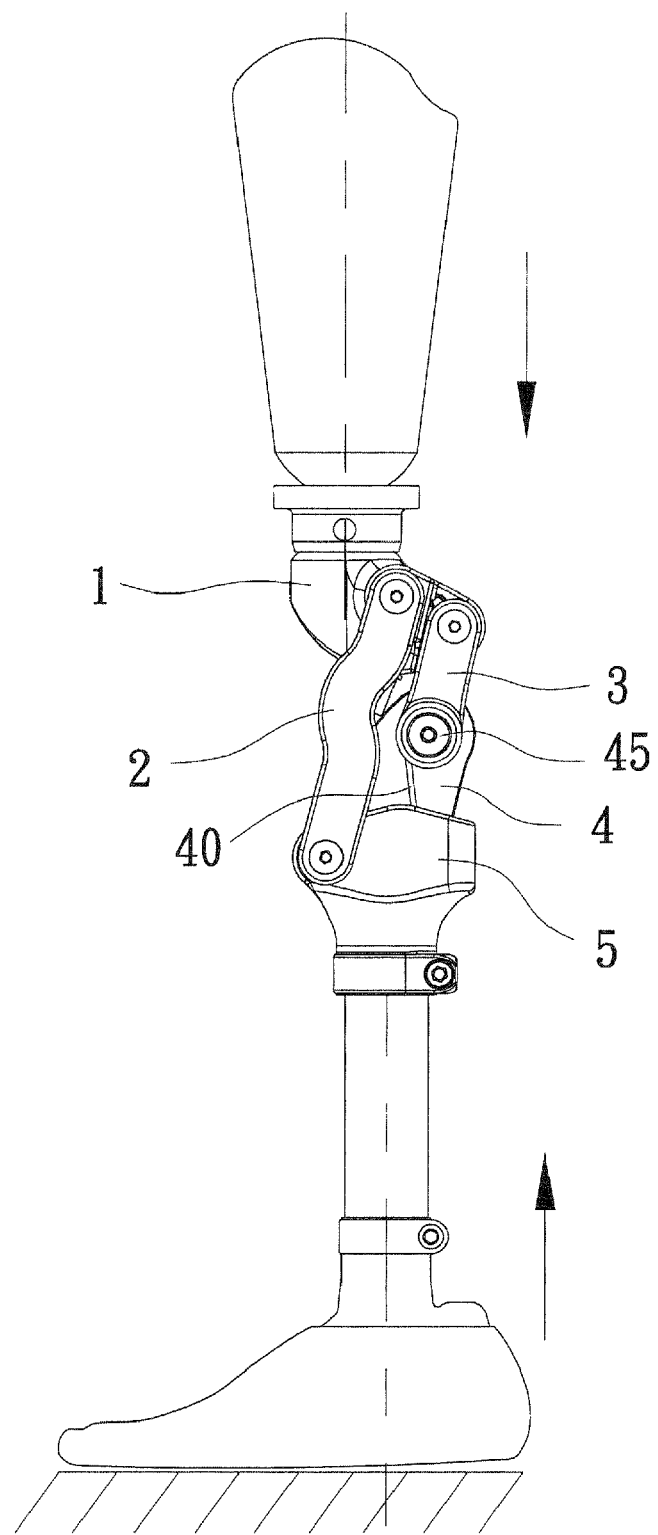
FIG. 1 is a side elevational view illustrating a standing condition of the present invention.
Figure 2:
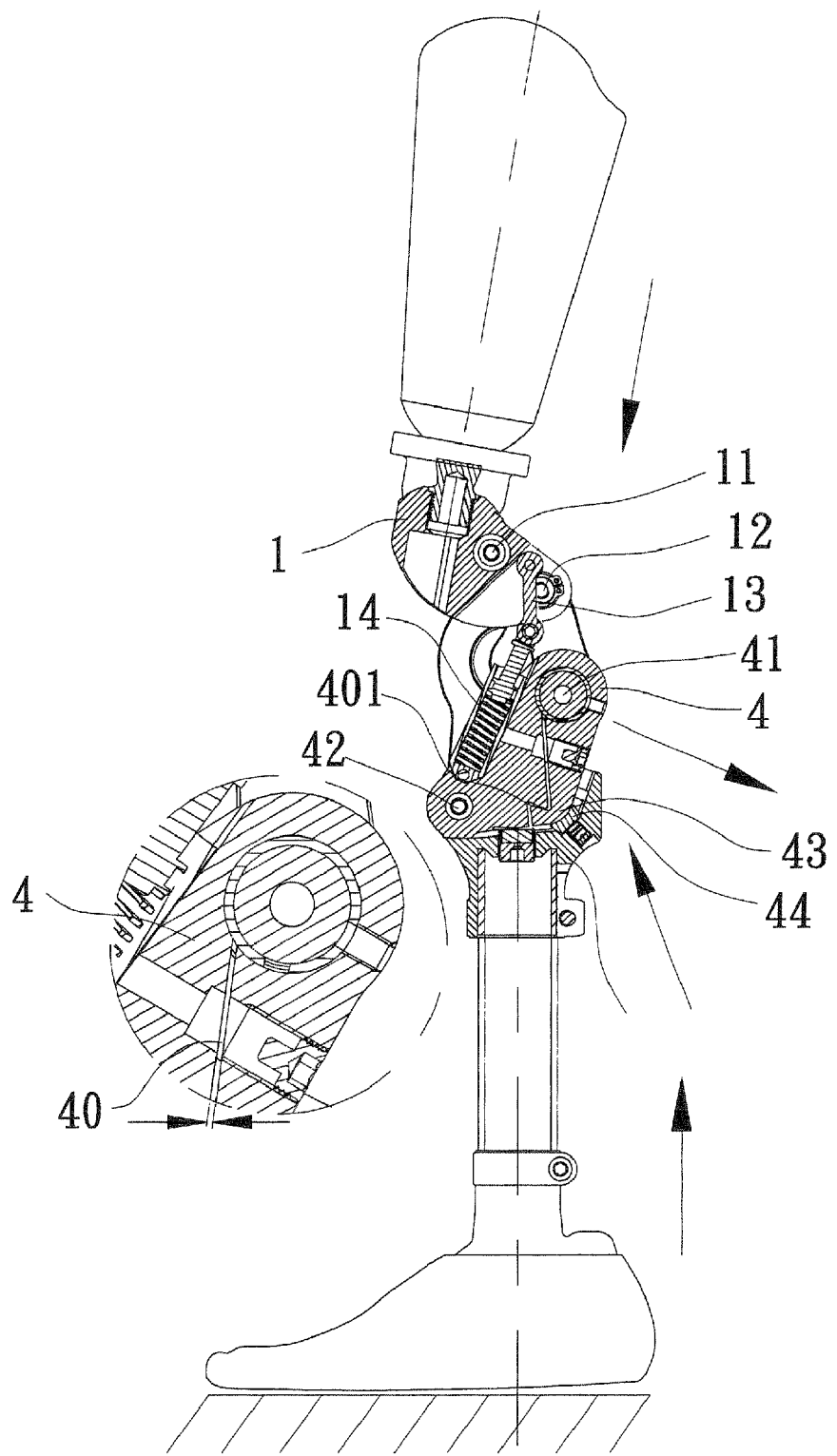
FIG. 2 is a schematic view showing an easy standing posture of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

An explanation of the structure and function of the present invention will be given for a preferred embodiment thereof with reference to the attached drawings in order to provide a more clear illustration of the principle of the present invention. The present invention provides a four-bar-linkage brake-included knee joint, which, as shown in FIGS. 1-6, comprises mainly a knee carriage 1, first links 2, second links 3, a clamp member 4, and a joint body 5.

As shown in FIGS. 1-6, the knee carriage 1 forms a front through hole 11 and a rear through hole 12 and is coupled, at an upper side thereof, to a prosthesis carrying barrel. Arranged inside the knee carrier 1 is an inner connection rod 13 that is connected to a cushioning assembly 14. The joint body 5 forms in a front portion thereof a joint body bore and is provided, at a rear portion thereof, with a compression block 44. The compression block 44 is structured in such a way that an amount of projection is adjustable. Two symmetric first links 2 have upper ends coupled to the front through hole 11 of the knee carriage 1 and lower ends coupled to the joint body bore. Two symmetric second links 3 have upper ends coupled to the rear through hole 12 of the knee carriage 1. The clamp member 4 is arranged at the inner sides of the first links 2 and the second link 3 and has an upper portion forming an upper through hole 41 and also forms a lower through hole 42 in a lower portion of a front portion thereof. The upper through hole 41 receives an axle 45 extending therethrough to couple lower ends of the second link 3. The lower through hole 42 is set in alignment with the joint body bore. The clamp member 4 is set in such a way that a back side thereof is in engagement with the compression block 44. The upper through hole 41 is provided with a gap 40, and the gap 40 is formed to comprise at least one bent segment 401 and extending downward from the upper through hole 41 to a bottom of the clamp member 4, whereby an opening of the gap is formed between the lower through hole 42 and the clamp back 43.

Figure 3:
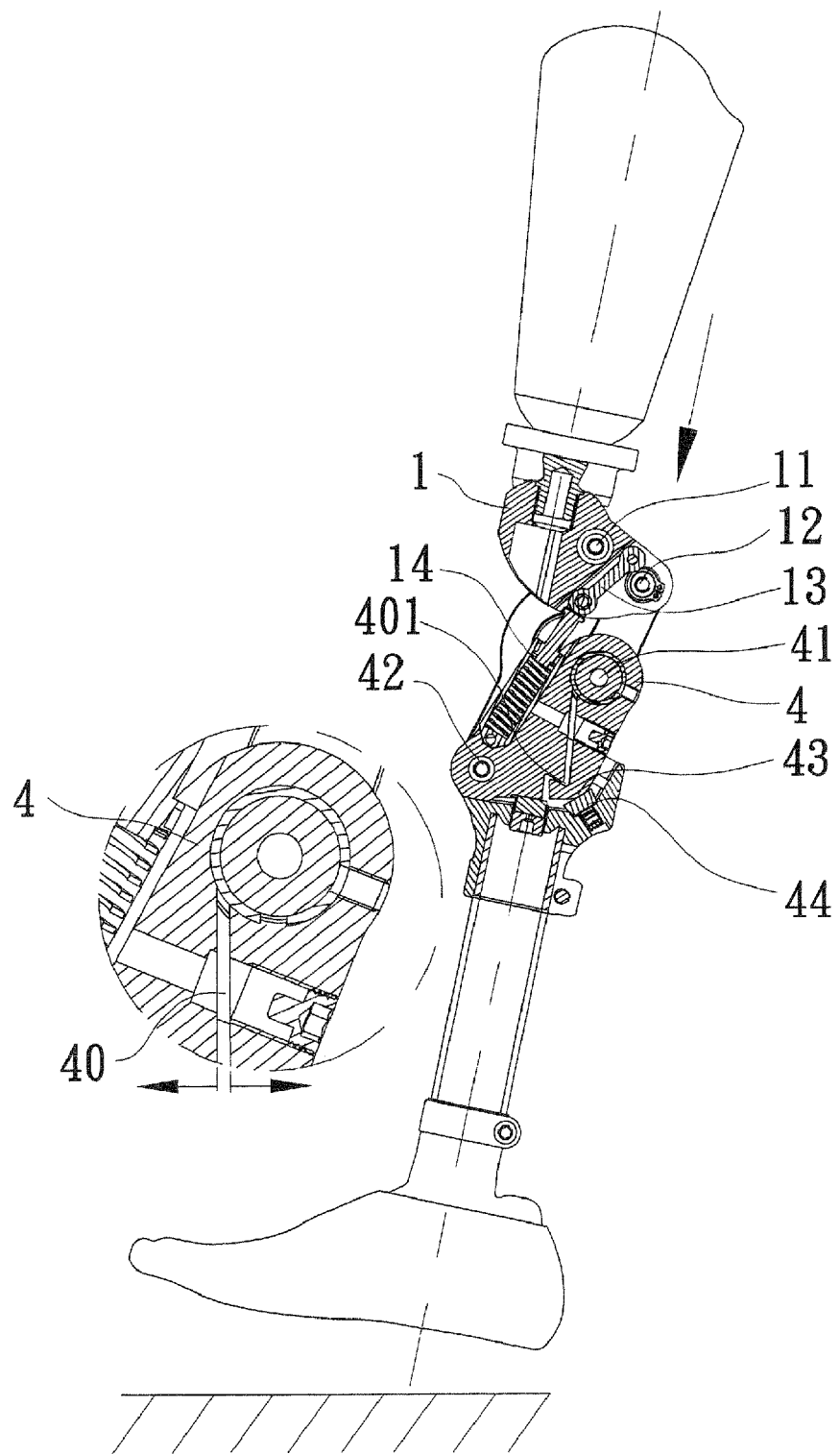
FIG. 3 is a schematic view showing a brake-released condition of the present invention walking on a horizontal surface.
Figure 4:
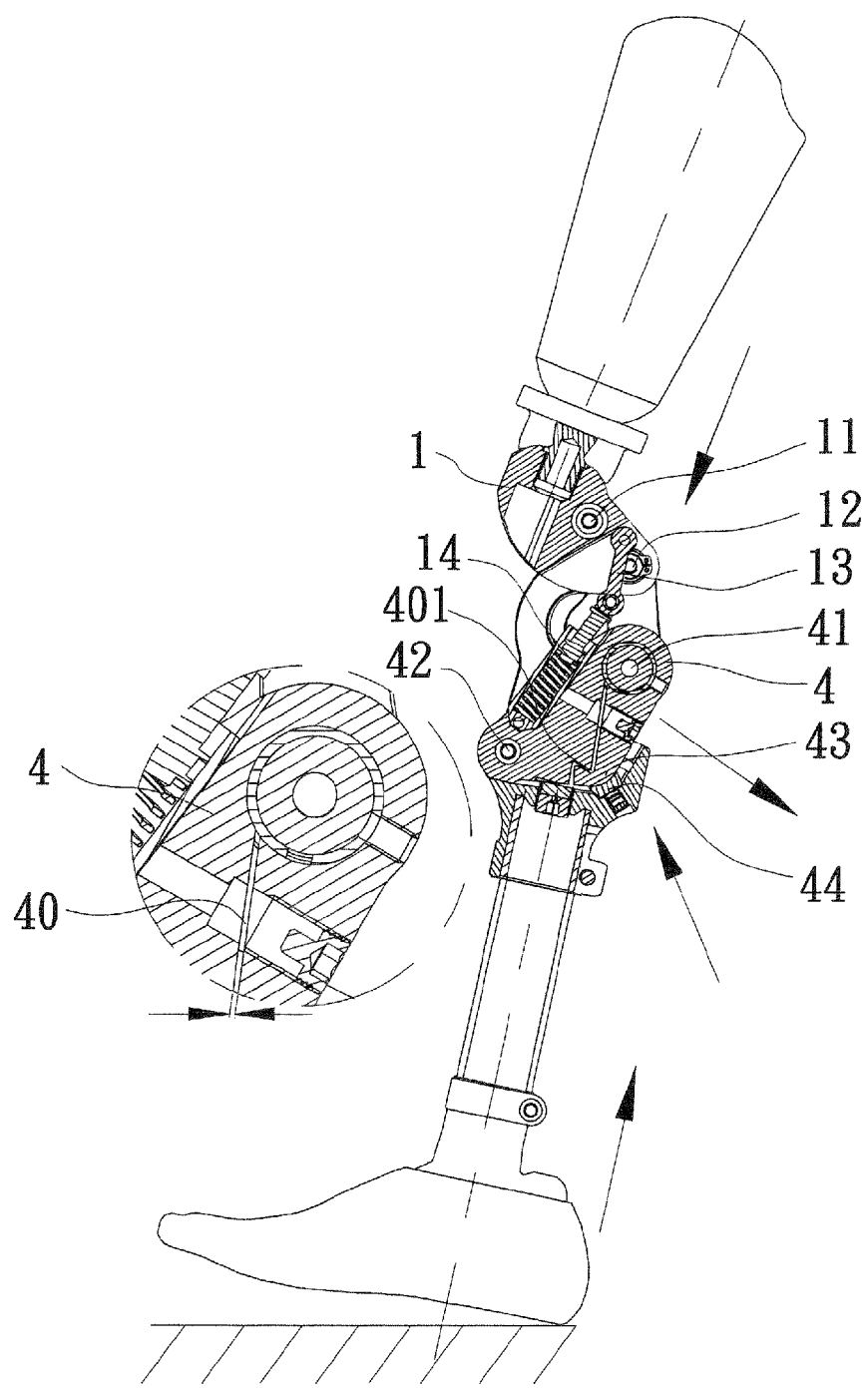
FIG. 4 is a schematic view showing a brake-engaged condition of the present invention walking on a horizontal surface.
Figure 5:
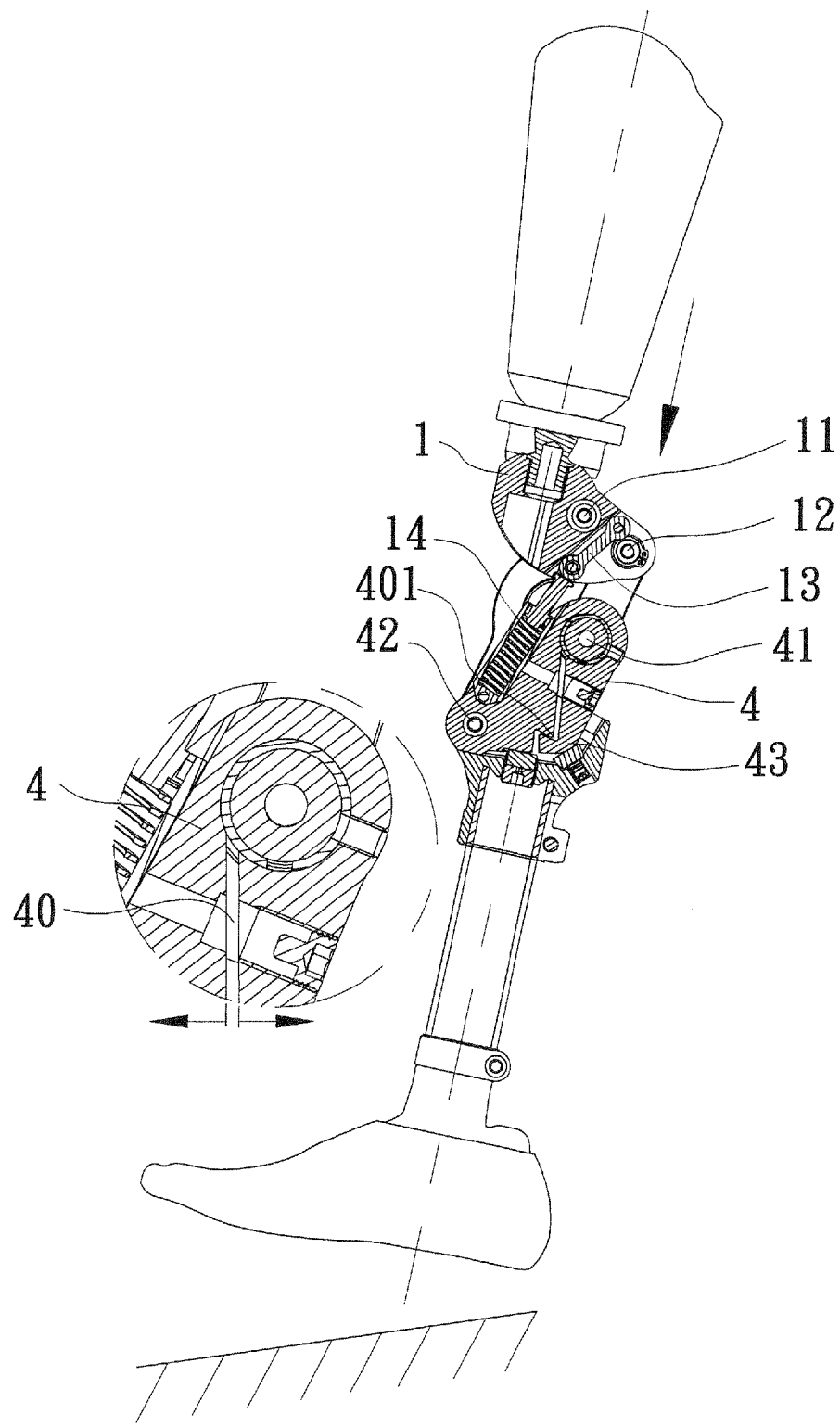
FIG. 5 is a schematic view showing a brake-released condition of the present invention walking on a downhill slope.
Figure 6:
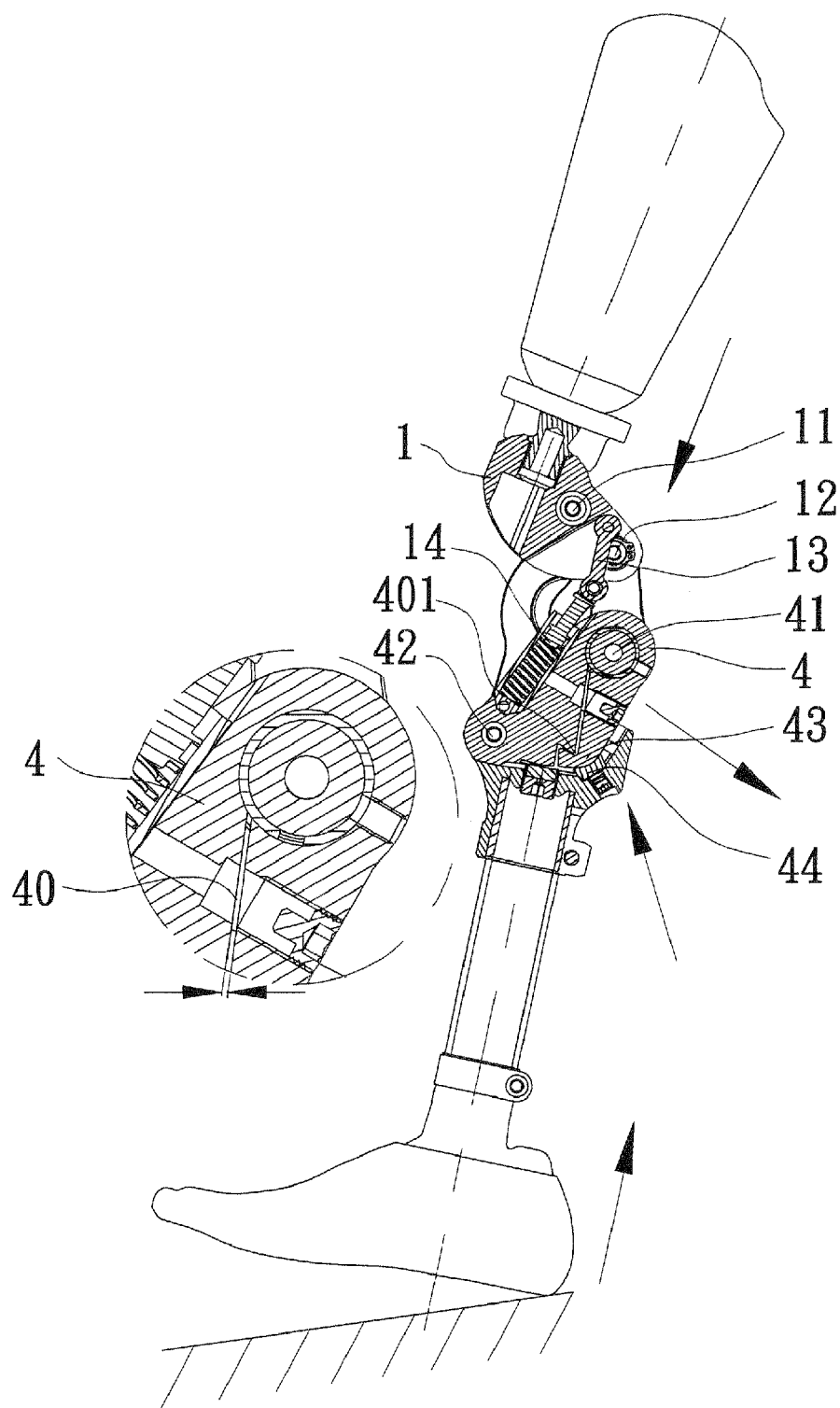
FIG. 6 is a schematic view showing a brake-engaged condition of the present invention walking on a downhill slope.
Figure 7:
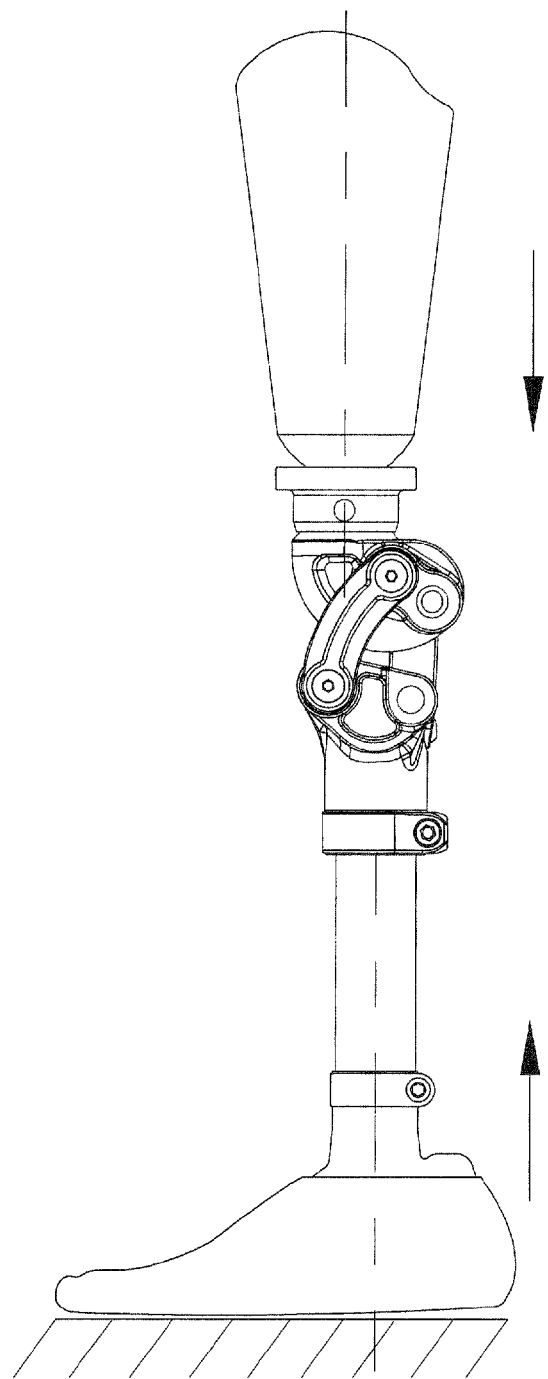
FIG. 7 is a side elevational view illustrating a standing condition of a conventional prosthesis.
Figure 8:
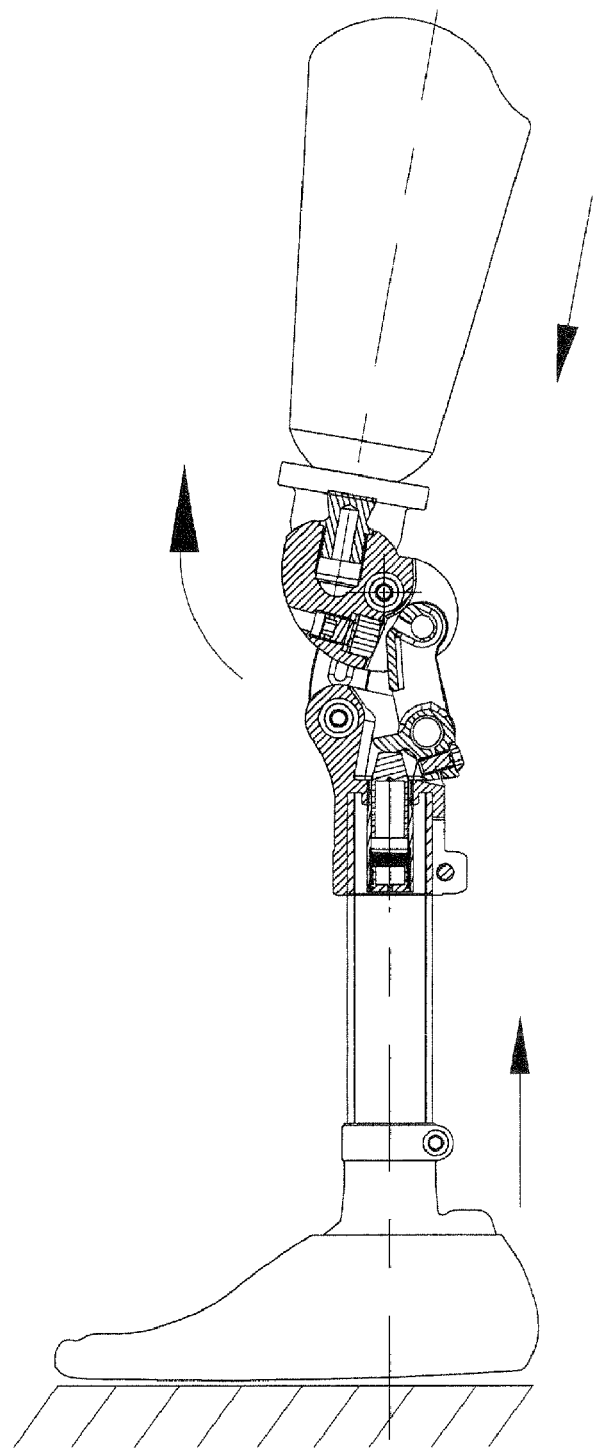
FIG. 8 is a schematic view showing an easy standing posture of the conventional prosthesis.
Figure 9:
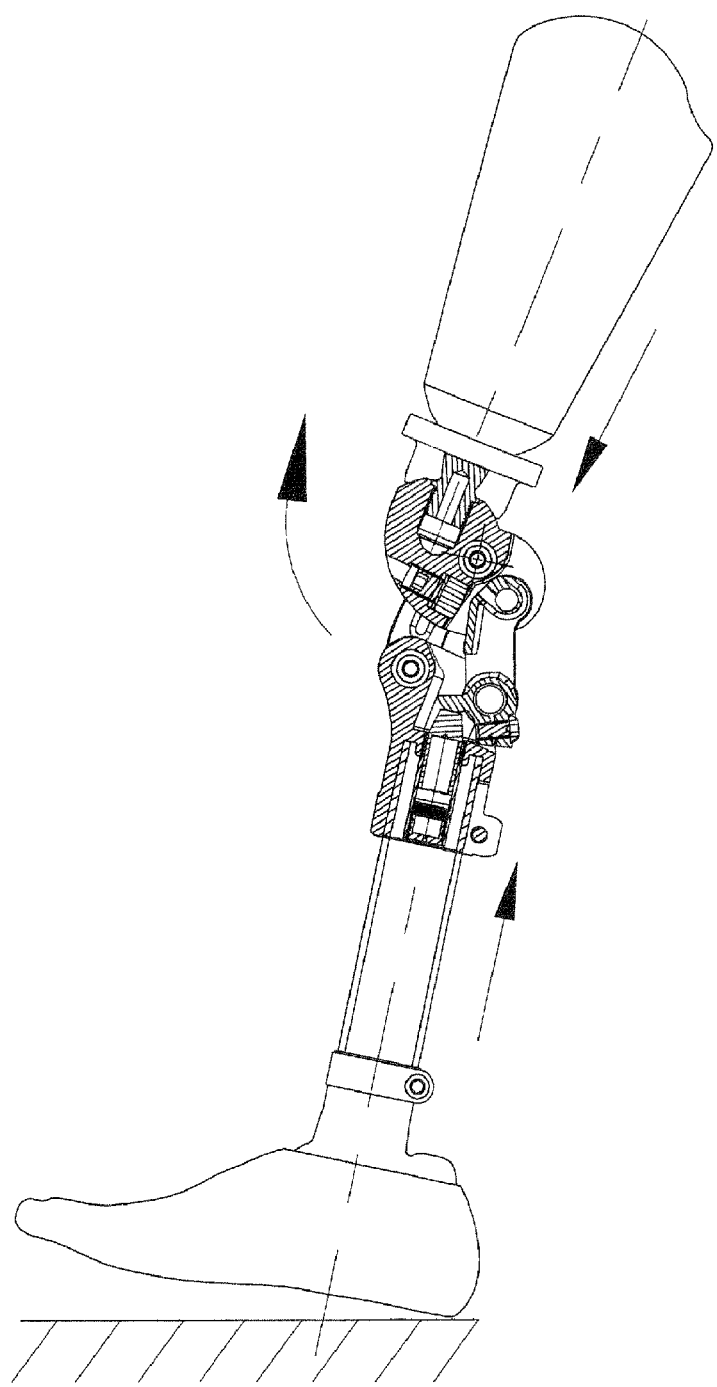
FIG. 9 is a schematic view showing the conventional prosthesis walking on a horizontal surface.
Figure 10:
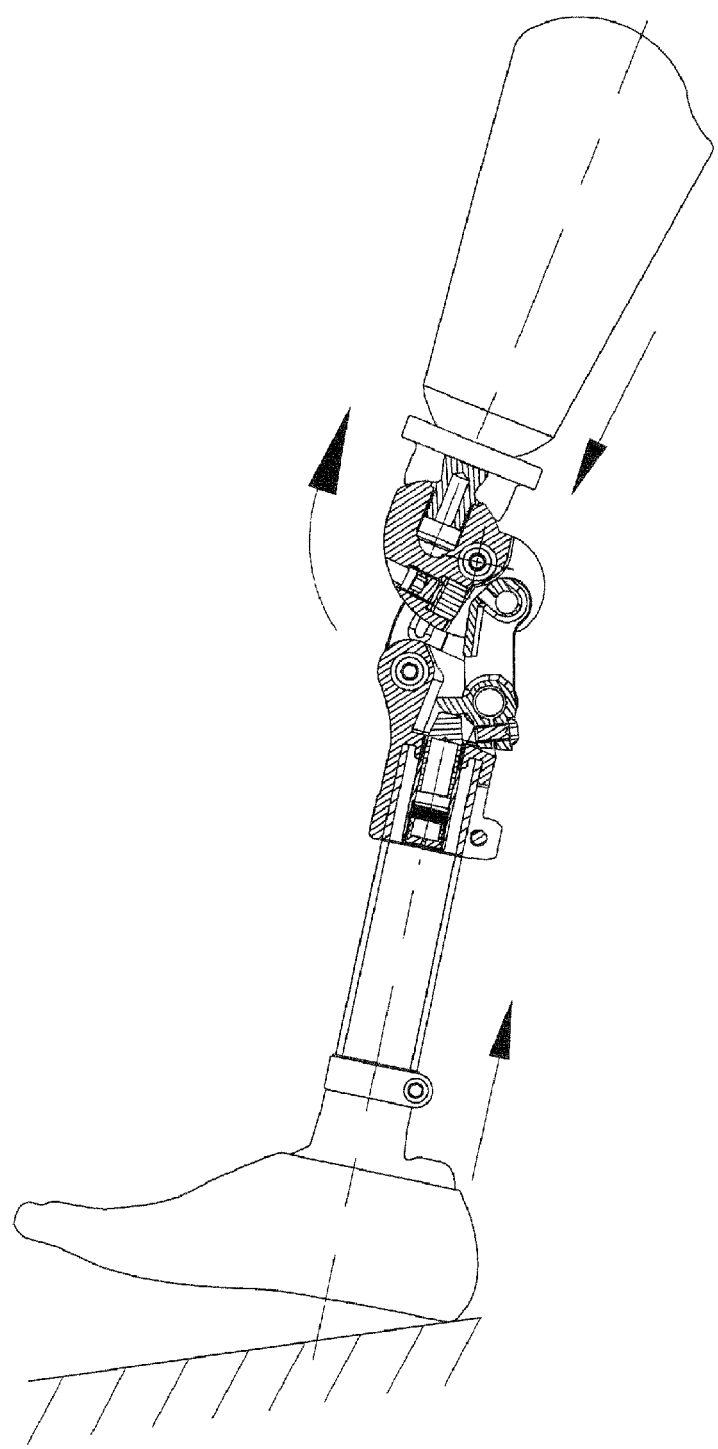
FIG. 10 is a schematic view showing the conventional prosthesis walking on a downhill slope.

Referring to FIGS. 2-6, the four-bar-linkage brake-included knee joint according to the present invention uses the gravity force of body weight or a reaction force induced by contact of the heel of the prosthesis with ground to reduce the gap 40 formed in the clamp member 4 to thereby constrain the rotation of the axle 45. Standing with the same posture for a long time may cause excessive local loading to the knee joint or cause excessive strain of muscles. When the user of the prosthesis wishes to take a different standing posture by slightly bending the knee or to shift the gravity center to the artificial limb side, the clamp member 4 according to the present invention can be used to cause the compression block 44 that is arranged in the rear portion of the joint body 5 to directly depress the clamp back 43 by using the body weight together with the force induced at the lower portion of the prosthesis and transmitted upward. Under this condition, the gap 40 formed in the clamp member 4 is reduced and the axle 45 is clamped to constrain rotation thereof. Thus, the easy standing posture shown in FIG. 2 may be realized. When the user of the prosthesis is walking on a horizontal surface or on a downhill slope, as shown in FIGS. 3 and 5 that illustrate a brake-released condition, where the heel of the prosthesis not yet in contact with the ground, the gap 40 of the clamp member 4 maintains in a non-reduced condition and is thus large to allow of free rotation of the axle 45 to complete a swing action of the limb. As shown in FIGS. 4 and 6, when the prosthesis is put into contact with the ground, the heel of the prosthesis generates a force in an upward direction, which causes the compression block 44 arranged in the rear portion of the joint body 5 to directly depress the back side of the clamp member 4 thereby reducing the gap 40 and tightly clamping and constraining the rotation of the axle 45. This prevents the prosthesis knee joint from sudden bending in the clockwise direction and thus causing potential risk.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A four-bar-linkage brake-included knee joint, comprising: knee carriage, which forms a front through hole and a rear through hole, and comprises an inner connection rod arranged inside the knee carriage to connect a cushioning assembly; a joint body, which has a front portion forming a joint body bore and has a rear portion in which a compression block is arranged; two first links, which have upper ends coupled to the front through hole of the knee carriage and lower ends coupled to the joint body bore; two second links, which have upper ends coupled to the rear through hole of the knee carriage; a clamp member, which is arranged at inner sides of the first links and the second links and has an upper portion forming an upper through hole and forms a lower through hole in a lower portion of a front portion thereof, the upper through hole receiving an axle extending therethrough to couple to lower ends of the second links, the lower through hole being substantially in alignment with the joint body bore, the clamp member being set in such a way that a back side thereof is in engagement with the compression block that is arranged in the rear portion of the joint body; the upper through hole being provided with a gap, which extends downward from the upper through hole to a bottom of the clamp member.

2. The four-bar-linkage brake-included knee joint according to claim 1, wherein the gap of the clamp member comprises at least one bent segment.

3. The four-bar-linkage brake-included knee joint according to claim 1, wherein the gap of the clamp member forms an opening between the lower through hole and the clamp back.

* * * * *